United States Patent [19]

Inman et al.

[11] Patent Number: 5,268,304
[45] Date of Patent: Dec. 7, 1993

[54] METHOD OF DETERMINING THE CONCENTRATION OF A CHEMICAL OF INTEREST IN A SOLUTION

[75] Inventors: Scott M. Inman, San Diego; Stephen H. Lieberman, La Mesa; Erik J. Stromvall, San Diego, all of Calif.

[73] Assignee: The United States of America as represented by the Secretary of the Navy, Washington, D.C.

[21] Appl. No.: 666,174

[22] Filed: Mar. 7, 1991

Related U.S. Application Data

[62] Division of Ser. No. 257,678, Oct. 13, 1988, Pat. No. 5,057,279.

[51] Int. Cl.$^5$ .............................................. G01N 1/70
[52] U.S. Cl. ..................................... 436/172; 436/56; 436/68; 436/178; 436/805; 422/56; 422/83; 422/86; 422/82.01; 356/317; 356/318; 356/417
[58] Field of Search ............... 422/56, 83, 86, 82.01, 422/91, 82.06, 82.07, 82.08, 82.09; 436/56, 68, 178, 805, 172; 356/317, 318, 417; 435/291, 808

[56] References Cited

U.S. PATENT DOCUMENTS

| 4,666,672 | 5/1987 | Miller et al. | 422/82.08 |
|---|---|---|---|
| 4,844,869 | 7/1989 | Glass | 422/82.08 |
| 4,892,383 | 1/1990 | Klainer | 422/82.06 |
| 4,929,562 | 5/1990 | Anderson et al. | 422/82.07 |
| 5,037,615 | 8/1991 | Kane | 422/82.08 |
| 5,043,285 | 8/1991 | Surgi | 422/82.06 |

OTHER PUBLICATIONS

Wangsa, J.; Arnold, M. A.; "Fiber-optic Biosensors Based on the Fluorometric Detection of Reduced Nicotinamide Adenine Dinucleotide", *Anal. Chem.*, 1988, 60, 1080–1082.

Munkholm, C; Walt, D. R.; Milanovich, F.P.; Klainer; "Polymer Modification of Fiber Optic Chemical Sensors as a Method of Enhancing Fluorescence Signal for pH Measurement", *Anal. Chem.*, 1986, 58, 1427–1430.

Fuh, MR S.; Burgess, L. W.; Christian, G. D.; "Single Fiber-Optic Fluorescence Enzyme-Based Sensor", *Anal. Chem.*, 1988, 60, 433–435.

Kulp, T. J.; Camins, I.; Angel, S. M.; Munkholm, C.; Walt, D. R.; "Polymer Immobilized Enzyme Optrodes for the Detection of Penicillin", *Anal. Chem.*, 1987, 59, 2849–2853.

Primary Examiner—James C. Housel
Assistant Examiner—Thomas E. Daley
Attorney, Agent, or Firm—Harvey Fendelman; Thomas Glenn Keough

[57] ABSTRACT

A method determines the concentration of a chemical of interest in a solution. A permeable membrane is placed in the solution and a ligand is exuded through the membrane to continually renew the ligand at the surface of the membrane which is in contact with the solution. Complexes of the ligand with the chemicals of interest are formed where the ligand renewed membrane is in contact with the solution. Illuminating the ligand renewed membrane with radiation from a distance from the membrane induces a fluorescence by the formed complexes on the ligand renewed membrane by the illuminating radiation. The fluorescence from the illuminated complexes on the ligand renewed membrane are detected from a distance from the membrane to provide a determination of the concentration of the chemical of interest in the solution.

3 Claims, 5 Drawing Sheets

METHOD OF DETERMINING THE CONCENTRATION OF A CHEMICAL OF INTEREST IN A SOLUTION

STATEMENT OF GOVERNMENT INTEREST

The invention described herein may be manufactured and used by or for the Government of the United States of America for governmental purposes without the payment of any royalties thereon or therefor.

This is a division of application Ser. No. 07/257,678 filed 13 Oct. 1988, now U.S. Pat. No. 5,057,279.

BACKGROUND OF THE INVENTION

Oceanographic and environmental concerns have increased the need for chemical sensing devices for the measurement of small-scale chemical features in aquatic environments. Conventional methods usually resort to two approaches; namely the collecting and analyzing the discrete samples in the laboratory and the use of sensors for in situ analysis. Disadvantages of both approaches for measuring nutrient distributions, species of geochemical interest and toxic chemicals are that they usually require cumbersome, individualized sampling techniques. Often the required sample handling and processing are time consuming, labor-intensive and may be subject to contamination and storage problems because some samples are often analyzed days to weeks after collection. In addition, such a delay does not lend itself well for mapping distributions of chemical constituents in dynamic aquatic environments. Presently available in situ sensors (mostly based on electrochemical measurements) are limited by several factors. Their response times may be slow, memory effects may persist, electrical interferences may compromise the results and some sensors are available only for a limited number of constituents. Optically based in situ sensors (optrodes) have relied upon chemical indicators (ligands) immobilized on the end of an optical fiber. When an analyte ion or molecule complexes with the ligand, fluorescence is induced or quenched. Such sensors have been used for measuring pH as reported by J. I. Petersen, et al in their article on page 864 in *Analytical Chemistry* 52 (1980) and D. M. Jordan, et al in their article on page 437 in *Analytical Chemistry* 59 (1987). Such sensors also have been found to provide indications in dissolved gases as reported by G. G. Vurek, et al on page 499 of *Anals Biomed. Enqr.* 11 (1983) and J. I. Peterson, et al's article on page 62 of *Analytical Chemistry* 56. Metal ions also have been sensed based on this type of a sensor as reported by S. Zhujun, et al in their article appearing on page 251 of *Anal. Chim. Acta* 171 (1985) and the L. A. Saari, et al article on page 667 of *Analytical Chemistry* 55 (1983). Such sensors typically involve the immobilization of a fluorogenic indicator on or near the end of a fiber optic cable. Excitation light and stimulation of the fluorophore and the resultant emission signal are both transmitted through the fiber optic cable. A problem with using immobilized ligands for real time sensing is that they are subject to photodegradation, leaching from the immobilization substrate, and there are difficulties with the immobilization chemistry. Most importantly with few exceptions, reversibility has not been demonstrated for immobilized ligand sensors, therefore they cannot be used for real time sensing.

Thus a continuing need exists in the state of the art for a sensor system that avoids the problems associated with immobilized ligand systems by forcing the ligand in a solution through a membrane and measuring the fluorescence or quenching that occurs at the membrane surface where the ligand interacts with the analyte solution.

SUMMARY OF THE INVENTION

The present invention directed to providing a fiber optic sensor that uses a pressurized membrane indicator delivery system for remotely detecting chemical species in solution. The apparatus provides an indication of the concentration of a chemical of interest in solution. A source of radiation creates an illuminating wavelength and a detector of radiation at fluorescence wavelengths are appropriately optically coupled to a fiber optic cable. A reservoir of a ligand is included that has the property to fluoresce at the fluorescence wavelength when the chemical of interest is complexed with the ligand and is radiated with the illuminating wavelength. A permeable membrane contacts the ligand on one side and the solution on the opposite side so that when a pressure source acts on the ligand, it exudes in controlled amounts through the permeable membrane to contact the solution and is complexed with the chemical of interest. The illuminating light causes the complexed compound to fluoresce and be detected. The fiber optic cable, optically coupled to the radiating source and the detector, has its opposite end spaced a suitable distance from the exuded ligand on the permeable membrane to allow the solution to pass between it and the membrane so that the fluorescence wavelength is created and properly detected.

An object of the invention is to provide a remote real-time sensor that has a reversible response.

Another object is to provide a real-time sensor in which a renewable indicator ligand passes through a membrane in contact with a solution and has a fast response time.

A further object of the invention is that the sensor system is uncomplicated and hence reliable for sensing small scale chemical features in solution.

Yet a further object is to provide a sensor that can be used in any liquid-like transmitting medium.

Another object is to provide a remote sensor relying upon a membrane and fiber optics to transmit light for the responsive sensing of phenomena in solution.

These and other objects of the invention will become more readily apparent from the ensuing specification when taken in conjunction with the claims and the appended drawings.

BRIEF DESCRIPTION OF THE DRAWINGS

FIGS. 4A and 4B are conceptual diagrams of the effect of pressure flow of indicator ligand through the ultrafiltration membrane; under low pressure as shown in FIG. 4A, the channeling of the ligand through the supporting Tyvec structure of the membrane is relatively minor resulting in fairly uniform coverage of the surface of the membrane that is in contact with the sample whereas FIG. 4B shows that at higher pressures, channeling of the ligand becomes more pronounced resulting in a decrease in the surface area of the membrane that supports the indicator ligand.

DESCRIPTION OF THE PREFERRED EMBODIMENT

Figure 1:
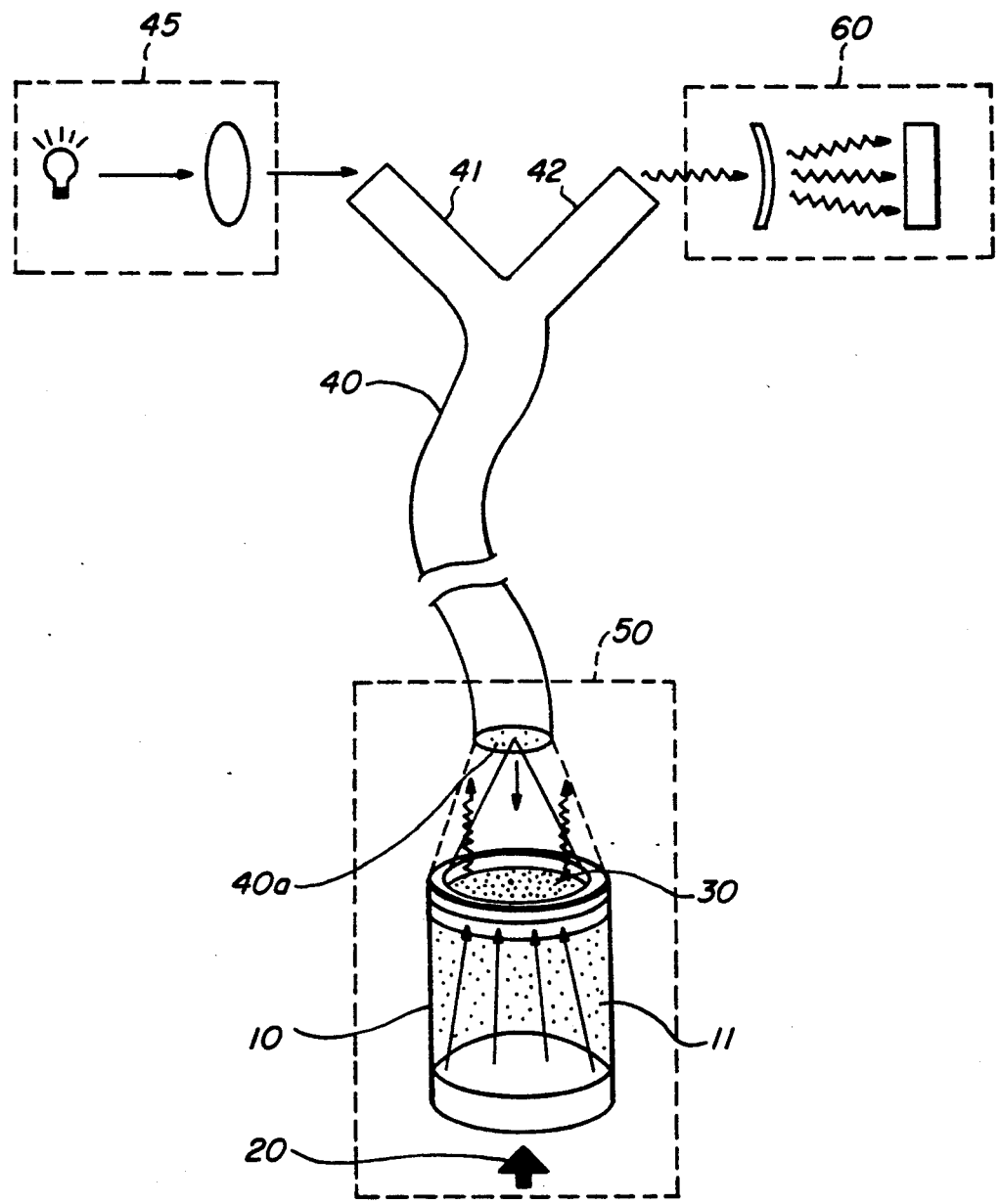
FIG. 1 shows an isometric depiction of a schematic representation of the invention.

The sensor system can be thought of as containing several main components. First of all a reservoir 10 of a ligand fluid 11 is acted on by a means for applying a pressure 20. The pressurized ligand fluid is forced to and through a membrane 30 that is illuminated by a fiber optic cable 40 that receives illuminating light from a appropriate source 45. The fiber optic cable also has fibers that channel the energy from fluorescent emissions on or near the surface of the membrane to a suitable detector arrangement 60 that provides responsive indications of fluorescent activity on the surface of the membrane.

The fluorescence emission spectra that were measured by detector arrangement 60 used an EG and G PAR optical multi-channel analyzer made up on a Model 1460 optical multi-channel analyzer with a Model 1463 detector controller controlling a Model 1420 diode array detector coupled to an EG and G Model 1232 compact spectrograph with a 300 grooves per millimeter poltographic grating and a 0.1 millimeter slit. The excitation light of source 45 was provided by a 75 watt xenon arc lamp mounted in a Model 02-A1000 arc lamp housing and powered by a Model 02LPS200 universal regulated PC arc lamp power supply, both of which are marketed by Photon Technology International, Inc., Princeton, N.J. The excitation filter used was a 360 nanometer band pass filter (marketed by Corion) FWHM of 11 nanometers and minimum peak transmittance of 30 percent.

Fiber optic cable 40 is a bifurcated fiber optic cable bundle made up on seven 325 micron core diameter UV-transmitting optical fibers manufactured by Guided Wave, Inc., Rancho Cordova, Calif. Of the bundle a single fiber was used to transmit the excitation energy from source 45 to membrane 30. The other six fibers receiving the fluorescence signal were arranged concentrically about the excitation fiber at the end of the fiber bundle contacting the sample and were arranged linearly at the end of the cable that was mated to the spectrograph of detector arrangement 60. Optionally one fiber optic cable may be used for both input of excitation light and reception of fluorescence emission, with use of appropriate beam splitting optics.

An important component of the indicator system is membrane 30 for it is the member through which ligand 11 is forced. As a consequence, it must be restrictive enough so that when pressure 20 is applied to ligand reservoir 10, ligand 11 flows through it in a controllable manner. In other words the membrane must sufficiently restrict ligand transport so that flow can be controlled by varying the pressure on the reservoir. In addition, the flow through the membrane must not vary significantly over time or spatially across the surface of the membrane so that the delivery of the indicator within the viewing volume of fiber optic 40 is constant over time. Several ultrafiltration membranes and filters were evaluated, ranging from 500 to 30,000 daltons molecular-weight. Ultrafiltration membranes such as those marketed by Amicon, Inc. for example Models YC05 and YMT3 as well as the 0.01, 0.1 and 0.2 micron pore diameter polycarbonate aerosol filters marketed by Nuclepore, Inc. An acceptable response was achieved with the ultrafiltration membranes of pore diameters of approximately 25 Å which are equivalent to a molecular weight cut-off of approximately 500 daltons and was provided by using the Amicon Model YC05 and YMT3.

Ligand 11 chosen for a representative demonstration of this inventive concept is a reagent-grade 8Hydroxyquinoline-5 sulfonic acid (8HQS) that was recrystallized from water. This particular ligand does not fluoresce appreciably unless it is complexed with one of several metal ions, notably Mg (II), Zn (II), Cd (II) and Ag (II). At a pH 8.1 zinc and magnesium complexes give UV absorption maxima at 360 nanometers and emission maxima at 517 nanometers. Since the sensing of metal ions in sea water is desired and magnesium is the dominant ion in sea water that forms complexes with 8HQS, sea water dilutions were used to evaluate sensor response in a sea water matrix. A typical concentration contained approximately 13,500 parts per million concentration of magnesium in the sea water.

Referring now to FIG. 2 a probe 50 integrates and holds as a functionally cooperative unit a number of the main system components referred to above. The probe is made of two units of stainless steel, an upper unit 51 having an internally threaded bore 51*a* for holding fiber optics 40 via an appropriately threaded surface on the optic's exterior, and a lower unit 52 that is also machined from stainless steel. A threaded reservoir holder 53 is provided with an appropriately threaded surface 53*a* to mate with a correspondingly machine surface on the inside of lower unit 52 so that an essentially cone-shaped reservoir 10' filled with ligand 11 is held closely adjacent membrane 30'. An O-ring 54 rests between the membrane and an annular rim 12 of the reservoir to keep ligand 11 from bypassing the membrane when pressure 20 is applied through a tubing section 55 of reservoir 10'. A pressurized gas source 56 is schematically shown and may be a gas cylinder controlled by a two-stage regulator via appropriate fittings for assuring that a proper pressure is exerted by ligand 11 on the abutting surface of the membrane 30'.

A stainless steel shaft 57 affixed to the upper and lower units separates them a predetermined distance such that the end 40*a* of fiber optic cable 40 is brought near enough the exposed surface of membrane 30' so that optical stimulation by at least one fiber 40*a'* will produce a detectable fluorescence for monitoring by at least one fiber 40*a''*.

Probe 50 is shown in cross-section and provides for greater understanding of this inventive concept in the flexibility afforded by this design.

The components 51, 52 and 53 are essentially cylindrically shaped but may vary to accommodate a particular use. In like manner the reservoir 10 or 10' can appear otherwise. Since the inside of upper unit 51 is threaded 51*a* and the outer surface of fiber optic cable 40 is correspondingly threaded, the separation from end 40*a* of the cable to membrane 30', can be varied by merely screwing the cable in or out and lower or raise the cable via the threaded interconnection.

Ligand reservoir 10' is shown in a tapered plastic configuration flared at the top and the flared annular rim 12 fits against o-ring 54 that, in turn, presses against membrane 30'. Ligand reservoir 10', o-ring 54 and membrane 30 prime sit inside the upper part of lower unit 52. When reservoir holder 53 is screwed into lower unit 52 via threaded part 53a, membrane 30' is pressed between an inwardly extending rim 58 of lower unit 52 and o-ring 54. Thus, ligand reservoir 10' is sealed against o-ring 54 and a pressure-tight fit is created between the membrane and the ligand reservoir.

Operation of the sensor system is an uncomplicated procedure after probe 50 is assembled and placed in a flowing sample. Membrane 30', o-ring 54 and ligand reservoir 10' are inserted into lower unit 52 and secured via reservoir holder 53. Fiber optic cable 40 is threaded into the upper unit 51 an appropriate amount for properly illuminating and receiving fluorescence. A ligand solution 11 is introduced into ligand reservoir 10' and pressure tubing 55 couples the reservoir to pressurized source 56. Pressure 20 from a gas cylinder for example, is applied to the system, forcing ligand 11 through the membrane. As indicator ligand 11 exudes from the membrane it complexes with the species of interest in the analyte solution. The complex is excited by light coming through source branch 41 and out fiber 40a' of bifurcated fiber optic cable 40 and fluorescence is induced or quenched on the surface of the ligand where it complexes with the ions of interest. The fluorescence signal is transmitted through sensor branch 42 via fibers 40a" and directed to the detection instrumentation in detector 60.

Figure 3:
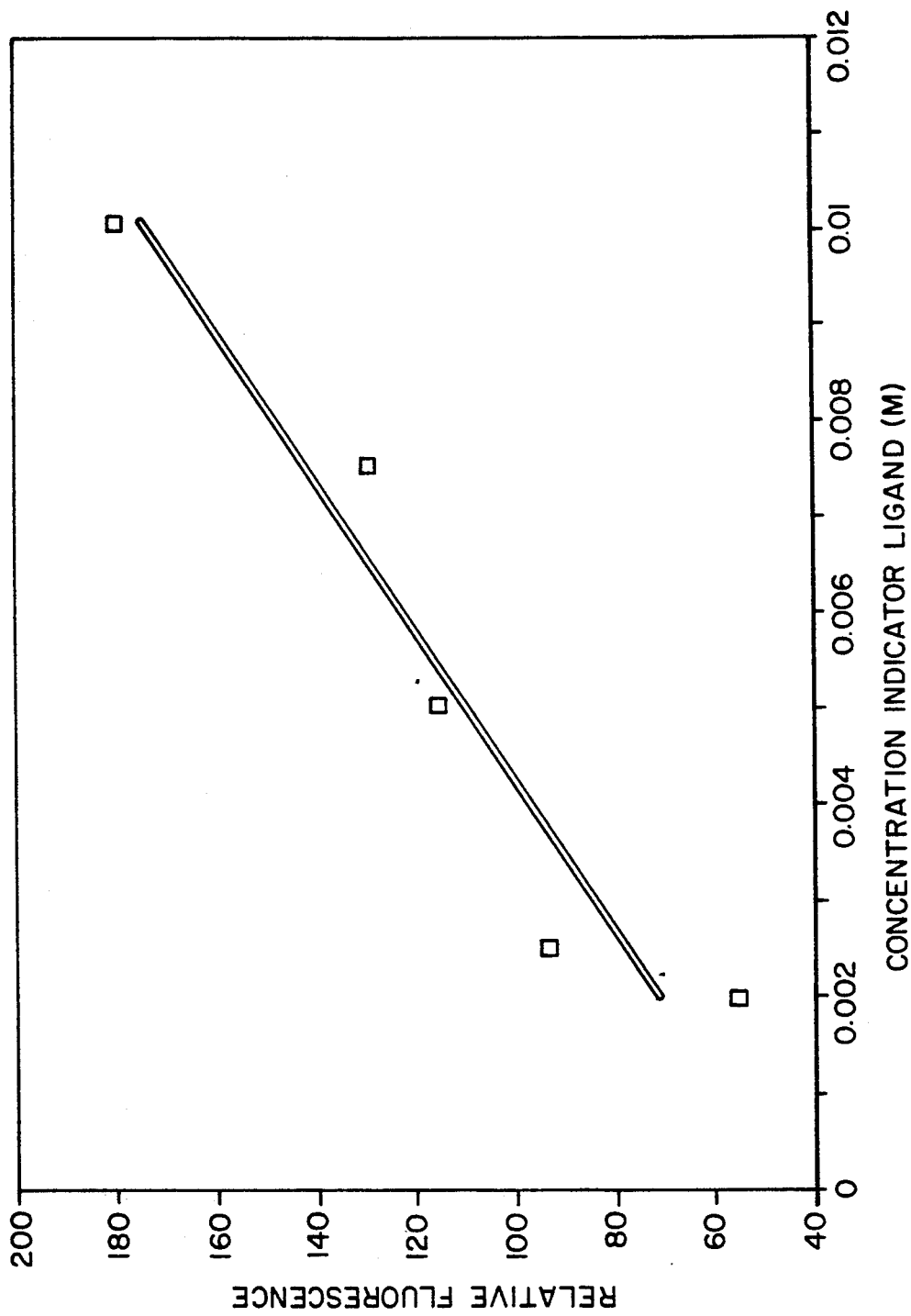
FIG. 3 shows a plot of fluorescence intensity versus concentration of indicator ligand in reservoir (20 percent sea water) pH 8.1 (sample flow rate 88 milliliters per minute).

The fluorescence response of the system was found to be a function of variations of the distance of the fiber optic cable end from the membrane surface, the pressure on the ligand reservoir, the flow rate of the analyte solution over the membrane and the concentration of ligand in the reservoir. The ligand concentration of 8HQS was varied from 0.002 to 0.01 M, see FIG. 3. The relative fluorescence signal increased 70 percent for a five-fold increase in the concentration of ligand in the indicator reservoir. At concentrations above the 0.01 mole the 8HQS solution showed a tendency to be unstable and precipitate; consequently 0.01 mole was considered the practical upper limit of this indicator solution.

For the purposes of verification a flow-through manifold with 20 percent sea water (pH 8.1) was used with a sample flow rate of 88 milliliters per minute. The distance of the end 40a of fiber optic cable 40 from membrane 30' was 2 millimeters. The pressure on the ligand reservoir was 5 psi, and the concentration of the indicator ligand in the reservoir was 0.01 mole. The manifold used for verification and not shown in the drawings was used to assure a flow rate of the 20 percent sea water to verify the effect that the above referred to variations induced in the response of the sensor system. From these tests it was determined that the optimal distance between the tip of the fiber optic cable and the membrane surface could vary from 2 to 22 millimeters and that for the above named ligand the maximum fluorescence signal was observed when the fiber optic cable was closest to the membrane surface. Two millimeters was found to be the smallest separation distance from end 40a of the fiber optic cable and the surface of membrane 30' that would not overly restrict the flow of sample between the fiber optic tip and the membrane surface. With respect to the ligand, it was found that the ligand flow through the membrane increased linearly with increasing pressure. However, in contrast, as pressure on the ligand reservoir was increased from 5 to 35 psi, the fluorescence signal detected decreased by 45 percent. This result was unexpected since it was thought that an increase in the amount of ligand passing through the membrane should have resulted in an increased complexation between the ligand and the ions of interest in the sea water sample, for example magnesium, and hence, should have increased the fluorescence signal. But this was shown not to be the case as will be explained with reference to FIGS. 4A and 4B.

Figure 4B:
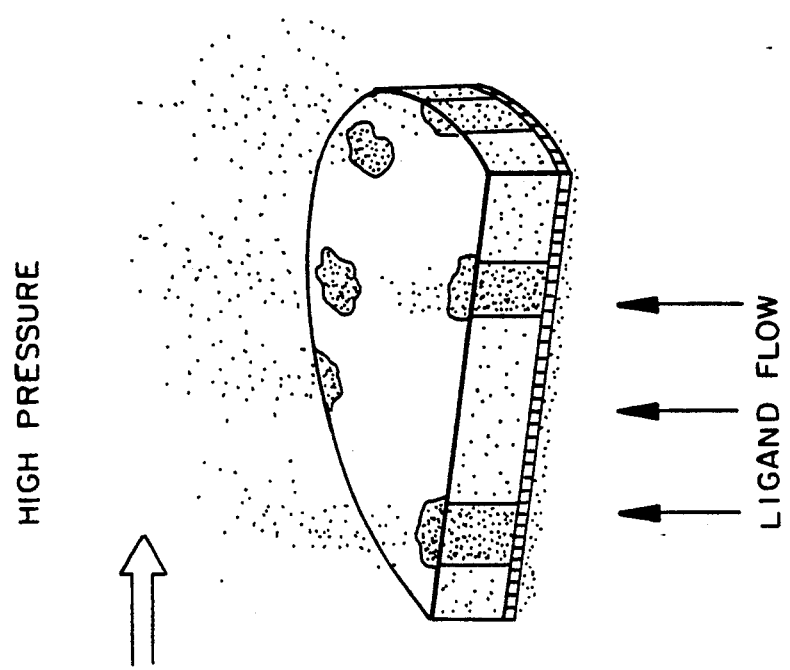
Figure 4A:
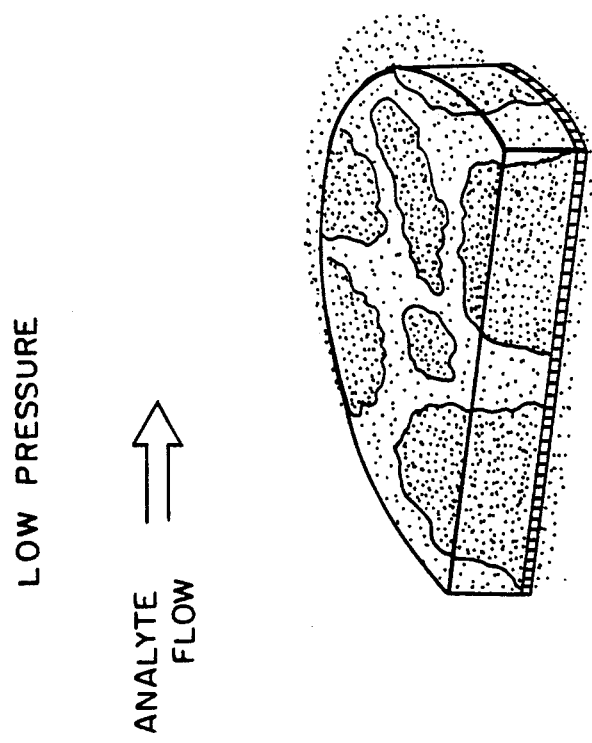

The response of the sensor as a function of ligand concentration, sample flow rate, pressure on indicator reservoir and distance of the fiber tip 40a from membrane 30' make apparent that the observed fluorescence signal is due to fluorescent complexes that reside on (or very close to) the membrane surface. FIGS. 4A and 4B present a conceptual model that accounts for the results. FIG. 4A shows that as the ligand is forced through the membrane it encounters two different filtering media (layers) on the membrane. The first is a more restrictive cellulosic layer that controls the flow rate; the second Tyvec layer channels the ligand solution to the surface. At the membrane-sample interface, analyte ions in the sample interact with the exuding ligand and complexation takes place. Fluorescence of the complex is stimulated by light coming from fiber 40a', of optic cable 40. Complexes are then removed by the flowing analyte solution.

At low membrane pressures, channeling through the Tyvec supportive structure is not excessive and the exuding ligand is distributed nearly uniformly over the surface of the membrane. As pressure on the indicator reservoir increases, channeling through the supportive Tryvec layer of the membrane increases and the indicator ligand tends to "jet" through small regions of the outer membrane, see FIG. 4B. This phenomena was confirmed by microscopic inspection of rhodamine exudation patterns. Increased channeling at higher pressures decreases the surface area over which complexation can occur and results in a reduction in the fluorescence signal. The idea that the observed signal is due to complexation at the membrane surface rather than in the conical volume of sample that extends from the probe tip to the membrane surface is consistent with the observation that as the flow rate of the analyte solution increased by more than a factor of 5, the measured fluorescence signal decreased by only 8 percent. If the fluorescence signal was from the indicator ligand-metal complex in the bulk solution, then the observed fluorescence signal should have decreased directly as a function flow rate. This is because increased sample flow rate past the membrane would have the same effect as diluting the indicator ligand.

In other words, the apparent contradiction between the increase in flow rate of indicator ligand through the membrane as a function of pressure and the observed decrease in fluorescence signal is apparent from FIG. 4B. As pressure on the membrane increases the ligand it tends to "jet" through smaller areas on the side of membrane 30' facing fiber end 40a of optic bundle 40. This reduces the surface area of the membrane in the field of view of fibers 40a' and 40a" of bundle 40 that contains indicator ligand capable of forming fluorescent complexes with the species of interest. Because the magnesium ion is the dominant cation in sea water that forms complexes with the indicator ligand 8HQS, the response of the sensor was first evaluated by making magnesium additions to distilled water.

The sample flow rate passing between end 40a of fiber optic cable 40 and membrane 30' also provide variations. A greater than five-fold increase in flow rate through the manifold and between the end of the fiber optic cable and membrane reduced the fluorescence signal by 8 percent. This suggests that the observed fluorescence signal is not determined by simple mixing of the indicator ligand into the bulk solution. If this was the case, the observed fluorescence signal should have decreased in proportion to the dilution factor resulting from the increasing volume of sample that passes over the membrane with increasing sample flow rate.

Figure 2:
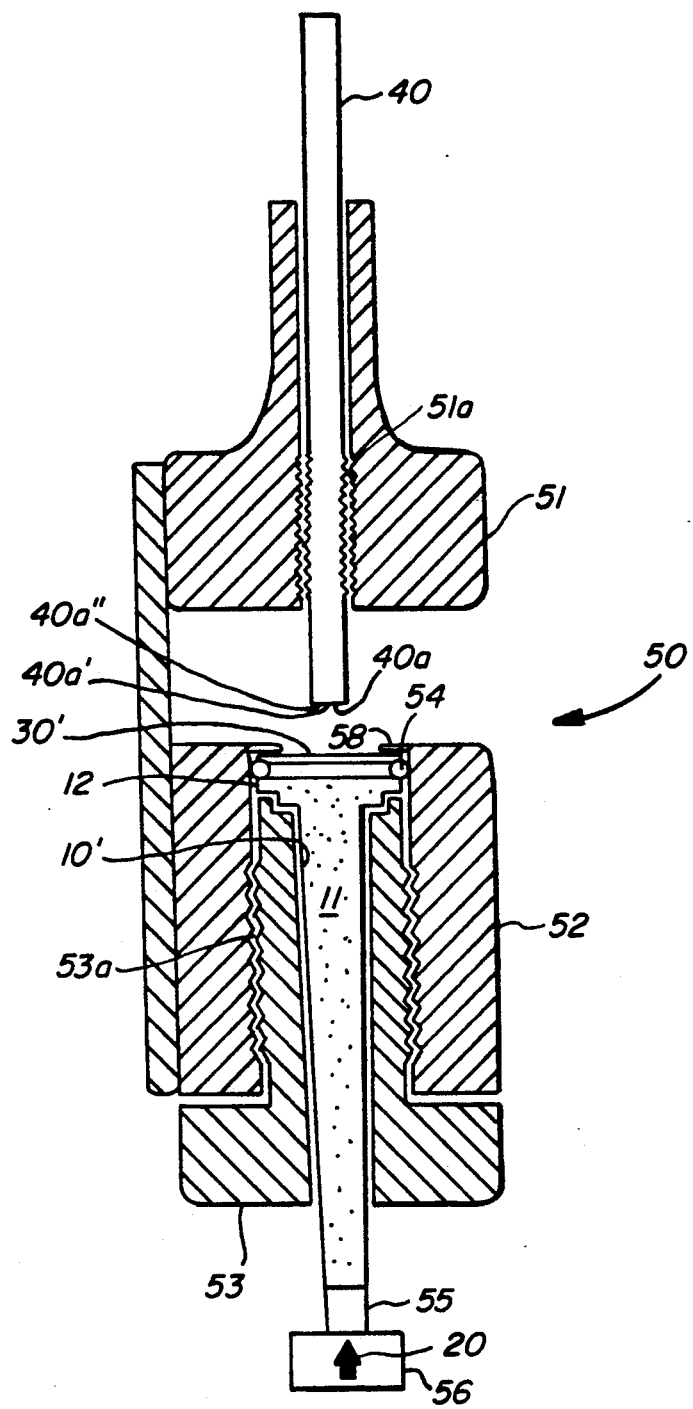
FIG. 2 is a cross-sectional detailed schematic of a pressurized membrane indicator system.

Operationally, probe 50 of FIG. 2 is suspended in the solution to be monitored, for example, from a research ship into flowing sea water. Fiber optic cable 40 and pressurized source 56 can terminate or be located on board with probe 50 being towed through or otherwise suspended in the water. The sea water flowing past the exuded ligand on the membrane will provide representative levels of fluorescence when properly illuminated.

Figure 5:
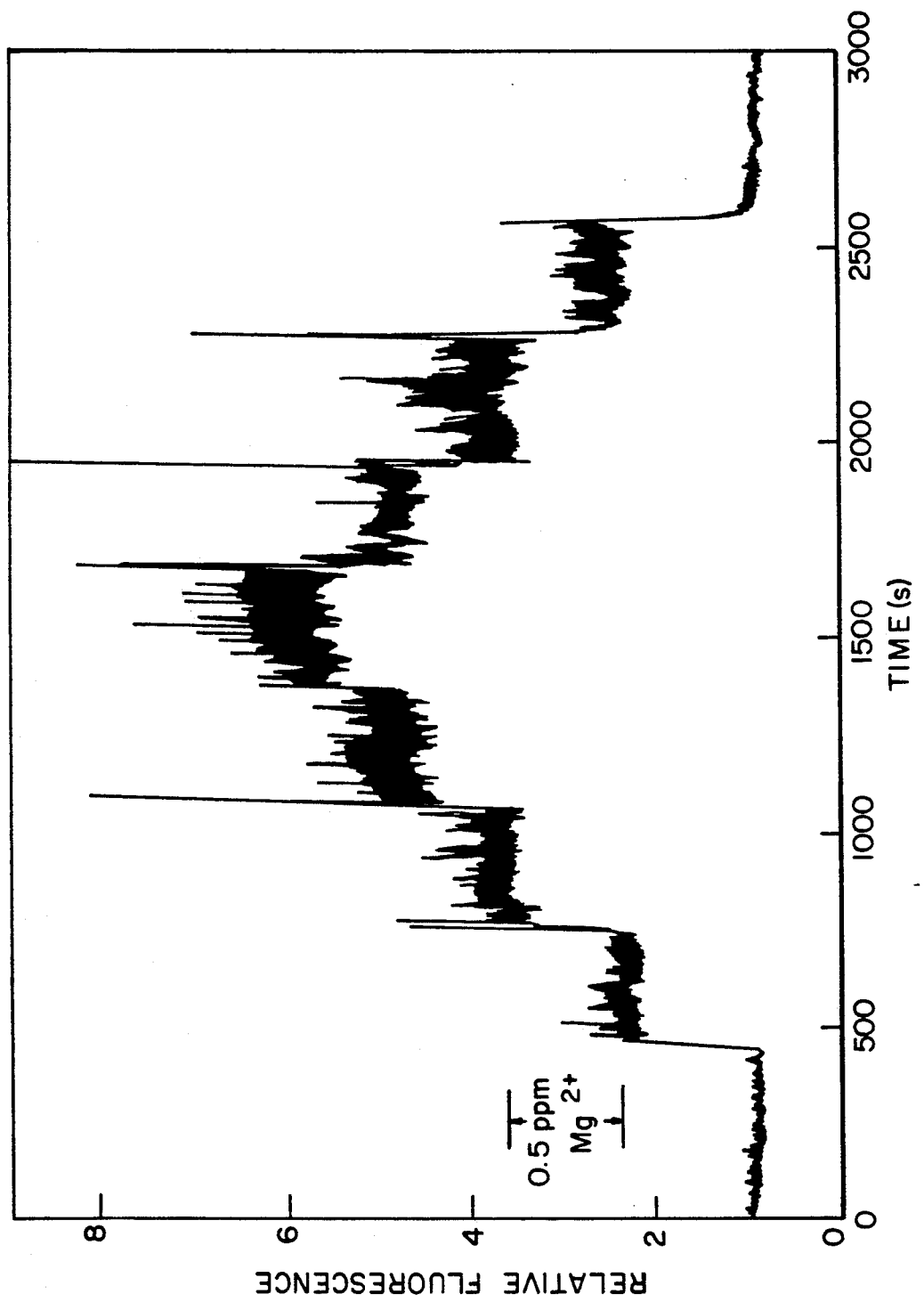
FIG. 5 depicts a time history of sensor fluorescence response in the flow-through manifold to 0.5 ppm increments of $Mg^{2+}$ ion in distilled water (pH 9.0).

FIG. 5 shows a time history of sensor response that resulted from pumping distilled water solutions that contained from 0.0 to 2.0 parts per million (in 0.5 parts per million increments) of $Mg^{2+}$ at pH 9.0 through a manifold containing the sensor. The results show that the sensor responded linearly for both increasing ($r^2 = 0.996$) and a decreasing ($r^2 = 0.988$) concentrations of Mg ion. The response of the sensor to ions in sea water was tested by pumping different dilutions of sea water through the manifold. A linear fluorescence response ($r^2 = 0.982$) was determined for sea water dilutions that ranged from 0 to 100 percent sea water. A linear response ($r^2 = 0.93$) was also demonstrated for the sea water dilutions in the range that is of interest for oceanographic applications (expressed in salinity units as 25 to 33 parts per 1,000). Although the indicator ligand 8HQS also forms fluorescent complexes with zinc, cadmium and silver, the molar concentration of magnesium in sea water is at least five orders of magnitude greater than any of these species. Thus, it is apparent that the observed response of the sensor in sea water is primarily due to the magnesium ion and that the sensor system could be used with the indicator ligand 8HQS as a fiber optic salinity sensor.

The membrane sensor system using an open-probe configuration such as that depicted in the cross-sectional representation of probe 50 in FIG. 2 have successfully proven this concept. This probe configuration is used for direct in situ measurements in the marine environment by lowering the fiber optic probe over the side of the survey vessel or in another application by the insertion of the probe into well-holes for ground water monitoring. The system was noted as avoiding bubble nucleation problems that may have otherwise occurred on the membrane and other surfaces when a sample was pumped through the manifold system. The open-probe monitoring showed standard deviation about the mean signal of about only ±1.04 percent. Optionally, laser excitation may be a useful means for improving sensitivity of the system.

The ability of the sensor to respond reversibly has been shown to be acceptable, thus enabling the device to be useful for real time measurements. Referring once again to FIG. 5, the tests conducted with magnesium in distilled water demonstrated that the membrane indicator system responds quickly to both increases and decreases in analyte concentration. In addition, comparison of the average fluorescence intensity at each magnesium concentration in FIG. 5 shows that there is no significant difference in the response of the sensor to changes in analyte concentrations measured for increasing magnesium concentrations, and for decreasing concentrations.

The response time for most other fiber optic based sensors, with the notable exception of those responding to small pH, range from tens of seconds to several minutes and seem to be so slow because most of the sensors employ some type of membrane to separate the immobilized indicator reagent from the bulk solution. As a consequence response times are often determined by a diffusion limited mass-transport step through the constraining membrane. In contrast the response time of this sensor of the inventive concept of the pressurized membrane sensor is fast because the indicator reagent is in direct contact with the analyte solution and response is only limited by the kinetics of the complexation reaction.

An important feature of the disclosed system is that it responds reversibly. It can detect both increasing and decreasing changes in target species concentration levels. Furthermore, the response time of the system is very fast, less than one second. These two characteristics allow the sensor to be used for real time sensor testing of small scale chemical features in solution. Most fiber optic sensors using immobilizing ligands are not reversible and electrochemical sensors have slow response times and memory effects.

Another advantage of the sensor is that it uses indicators in the form of a solution, not a solid, providing a universal delivery system. Because the indicator is in a solution, it is possible to modify the chemical composition of the solution changing the sensing environment to favor desired chemical reactions. Almost any solution can be used in the ligand reservoir allowing the use of hundreds of reagents currently available for analysis of chemical species. Many organic as well as water soluble reagents can be used with the sensor. This feature taken in consideration with the simple design of the sensor makes it easy to use by simply inserting a membrane, filling the reservoir with the selected ligand and pressurizing it. The proper illuminating wavelengths and fluorescence detectors complete the system. Since the sensor uses light signals, it avoids the use of a reference electrode and other electrical problems. The use of fiber optics allows the sensor to be used remotely and in real time. Its uncomplicated design facilitates miniaturization and mass unattended use.

The sensor is not restricted to aquatic environments but can be used in any liquid light-transmitting medium that is nondestructive to the materials the sensor is made of. Use in environments where the flow rate or pressure varies requires the sensor use an internal fluorescent standard to monitor the reagent flow from the membrane.

Materials of construction for the sensor can vary considerably. The membrane portion can be constructed of any material that will allow controlled flow of reagent when pressure is applied to the reservoir. The flow should such that the reagent exudation is uniformly distributed over the area viewed by the optical excitation and emission fibers. In addition to conventional filters and membranes, materials such as porous glass could be used. The sensor body can be constructed of any material rigid enough to assure that the fiber optic cable and membrane configuration does not change and firm enough to allow sufficient compression of the membrane and reservoir assembly to prevent reagent leakage.

Configuration of the reservoir and membrane size and shape may vary as well as the orientation of the fiber optic cable to the membrane surface. What is unique about the sensor is that the sensing phenomena is occurring largely on the surface of the membrane through which a liquid chemical reagent is being forced. Response is rapid and reversible because the indicator reagent is continually renewed from the reservoir and continually removed by solution effects in the analyte medium. Variations in the configuration of the apparatus for particular applications could be made without violating the principles of the sensor system.

Although the optics for the source, detector and fiber optics have not been detailed, it is apparent that suitable lens and focusing arrangements are includable as needed and will be within the purview of a routineer. Remote light sources and sensors may be used for illuminating and detecting with appropriate light coupling other than the fibers.

Obviously, many modifications and variations of the present invention are possible in the light of the above teachings. It is therefore to be understood that within the scope of the appended claims the invention may be practiced otherwise than as specifically described.

We claim:

1. A method of determining the concentration of a chemical of interest in a solution comprising:

placing a permeable membrane in contact with said solution;

exuding a chemical indicator from a reservoir containing said chemical indicator through said membrane to provide a continuously renewable supply of said chemical indicator at the surface of said membrane with said chemical indicator in contact with said solution, said exuding includes a pressurizing of said reservoir containing said chemical indicator communicating with said membrane thereby causing said chemical indicator to be exuded through said membrane in controlled amounts;

forming complexes of said chemical indicator with said chemical of interest by contacting said continuously renewable supply of said chemical indicator with said solution at the surface of said membrane;

illuminating continuously renewable supply of said chemical indicator at the surface of said membrane with radiation thereby concurrently inducing fluorescence of said complexes at said membrane surface; and inducing fluorescence of the formed complexes with said continually renewing said ligand at the surface of said membrane by the illuminating radiation; and detecting said fluorescence from the complexes with said continuously renewable supply of said chemical indicator at the surface of said membrane.

2. A method according to claim 1, wherein said illuminating and said detecting steps are performed by at least two optical fibers that coalesce towards said membrane.

3. A method according to claim 1, wherein said illuminating and detecting are performed by one single fiber optic cable having beam splitting optics.

* * * * *